United States Patent [19]

Fruchey et al.

[11] Patent Number: 4,485,047

[45] Date of Patent: Nov. 27, 1984

[54] COPPER AND MANGANESE OXIDATION CATALYSTS RECOVERY FROM AQUEOUS SOLUTIONS

[75] Inventors: Olan S. Fruchey; Edward M. de la Garza, both of Corpus Christi, Tex.

[73] Assignee: Celanese Corporation, New York, N.Y.

[21] Appl. No.: 466,448

[22] Filed: Feb. 15, 1983

[51] Int. Cl.³ ............................ C11C 1/00; C07F 1/08; C07F 11/00
[52] U.S. Cl. ..................................... 260/413; 260/414; 260/429 R; 260/438.1; 562/531
[58] Field of Search ............... 260/413 R, 414, 429 R, 260/438.1; 252/413; 560/531

[56] References Cited

U.S. PATENT DOCUMENTS

| | | | |
|---|---|---|---|
| 3,846,460 | 11/1974 | Fite | 260/439 R X |
| 4,246,185 | 1/1981 | Wood | 260/413 R |
| 4,257,913 | 3/1981 | Fischer | 260/429 R X |
| 4,289,708 | 9/1981 | Scott et al. | 260/413 R |

*Primary Examiner*—Helen M. S. Sneed
*Attorney, Agent, or Firm*—L. I. Grim; M. Turken

[57] ABSTRACT

A process is described for recovering water soluble copper and manganese compounds from an aqueous solution by reacting the copper and manganese compounds with saturated aliphatic monocarboxylic acids containing 5 to 9 carbon atoms at elevated temperatures forming cupric and manganous alkanoates containing 5 to 9 carbon atoms, and simultaneously removing the water by distillation in the presence of sufficient oxygen-containing gas to prevent the copper from plating on the distillation equipment, recovering the cupric and manganese alkanoates.

7 Claims, 1 Drawing Figure

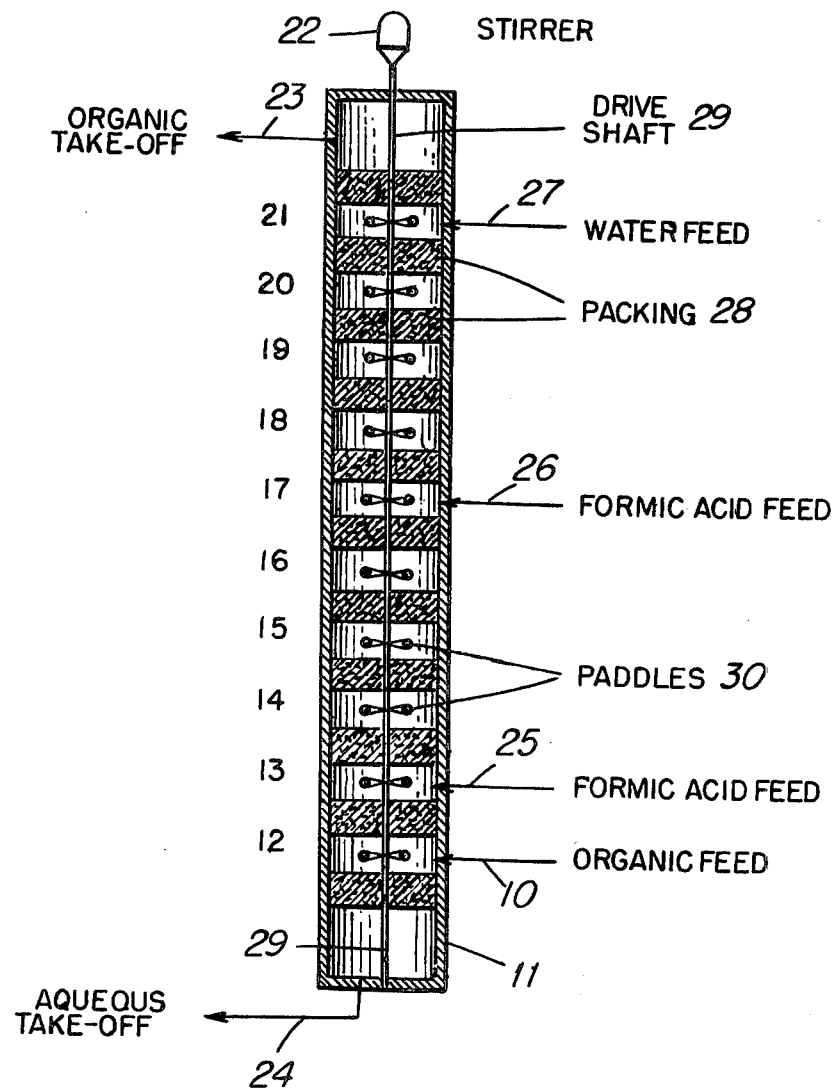

COPPER AND MANGANESE OXIDATION CATALYSTS RECOVERY FROM AQUEOUS SOLUTIONS

This invention relates to a process for the recovery of copper and manganese compounds used as catalysts for the oxidation of saturated aliphatic aldehydes to saturated aliphatic monocarboxylic acids containing 5 to 9 carbon atoms, from an aqueous solution. More specifically, the catalyst metal ions, copper and manganese, extracted from the saturated aliphatic monocarboxylic acids containing 5 to 9 carbon atoms in the form of cupric formate and manganous formate in an aqueous solution, can be recovered by reacting the cupric and manganous formate with a saturated aliphatic monocarboxylic acid containing from 5 to 9 carbon atoms at elevated temperatures to form the corresponding cupric and manganous alkanoates, and simultaneously removing the water and formic acid by distillation in the presence of sufficient oxygen-containing gas to prevent copper from plating on the distillation equipment, and recovering the cupric and manganous alkanoates. These compounds, in combination, are suitable for use as oxidation catalysts and in particular, in the production of saturated aliphatic monocarboxylic acids from their corresponding aldehydes.

BACKGROUND OF THE INVENTION

When oxidizing organic saturated aliphatic aldehydes containing 5 to 9 carbon atoms to the corresponding monocarboxylic acids, an important objective is to obtain sufficiently high yields and product efficiencies at high enough conversion levels in a single pass, to avoid recycle of significant amounts of unreacted starting materials. Catalysts comprising copper and manganese facilitate this objective, since they result in the production of larger amounts of acid per pass than do manganese catalysts alone. However, a disadvantage often resulting from the use of copper-manganese catalysts in aldehyde oxidation processes, particularly ones in which the reaction product must be distilled to recover the desired product, is the plating out of copper in the distillation apparatus. Plating out, of course, can lead to undesirable mechanical problems, including erosion of reboilers and pump impellers and rapid pump seal failures.

Copending U.S. application Ser. No. 345,890 filed Feb. 4, 1982, assigned to Celanese Corporation claims a process of the type described utilizing a copper-manganese catalyst. This process provides commercially attractive high carbon efficiencies of aldehyde to acid at high aldehyde conversions. A single stage or two stage liquid phase reactor system generally gives sufficiently high aldehyde conversions so that recycle of unreacted aldehyde is, in most cases, unnecessary. However, when the reaction mixture is distilled to recover the acid, copper tends to precipitate and plate out on the distillation apparatus unless something is done to prevent it.

One means of overcoming this problem is to add relatively pure oxalic acid to precipitate copper and manganese from the reaction mixture as their oxalates, prior to the distillation step. This process is described in U.S. Pat. No. 4,289,708, issued Sept. 15, 1981 to Scott et al and assigned to Celanese Corporation. Copper and manganese can also be separated from the reaction mixture by precipitating them, again as their oxalates, by adding an aqueous oxalic acid solution. In this case, the manganese and copper oxalates precipitate into the aqueous phase, which can be readily separated from the organic acid product by decantation. The acid can then be further purified by distillation. However, aqueous oxalic acid cannot be used satisfactorily to treat mixtures containing valeric acid due to this acid's high solubility in water. This process is described in U.S. Pat. No. 4,246,185, issued Jan. 20, 1980 to Wood, Jr. and assigned to Celanese Corporation.

Copending application Ser. No. 466,447 assigned to the same assignee and filed concurrently with this application describes a process for extracting copper and manganese catalysts from a water-immiscible organic phase comprising a saturated aliphatic monocarboxylic acid containing 5 to 9 carbon atoms. The catalyst metal ions, copper and manganese, are reacted with aqueous formic acid to form the cupric and manganous formates which are highly soluble in water and have a low solubility in the water-immiscible organic phase comprising $C_5$–$C_9$ saturated aliphatic monocarboxylic acid. Since valeric acid is very soluble in water, valeric acid containing manganese and copper can be combined with a water-immiscible organic solvent such as hexene and/or heptene to form a water-immiscible organic phase containing valeric acid in the presence of water. On the addition of aqueous formic acid to the organic phase containing the valeric acid, manganese and copper ions, manganous and cupric formates being highly soluble in water will form and be removed from the organic phase into the aqueous phase. $C_6$–$C_9$ saturated aliphatic monocarboxylic acids are immiscible in water and will form the organic phase without additional organic solvents. Two phases, an organic phase and an aqueous phase, are formed. The organic phase comprising the monocarboxylic acid, is substantially free of copper and manganese and the acids can be separated from the aqueous phase. The $C_5$–$C_9$ saturated aliphatic monocarboxylic acid can then be purified and readily recovered by distillation. However, the invention claimed in this application does not include the recovery of copper and manganese from the aqueous phase.

It is the purpose of this invention to recover the copper and manganese metals from the aqueous phase in the form of cupric and manganous alkanoates containing 5 to 9 carbon atoms. These alkanoates, in combination, can be used as oxidation catalysts and especially in the production of $C_5$–$C_9$ saturated aliphatic monocarboxylic acids by the oxidation of their corresponding aldehydes.

THE INVENTION

This invention comprises a process for recovering water soluble cupric and manganous ions used as oxidation catalysts, present in water, by reacting a saturated aliphatic monocarboxylic acid containing 5 to 9 carbon atoms with the cupric and manganous compounds at temperatures from about 190° C. to about 240° C. forming cupric and manganous alkanoates containing 5 to 9 carbon atoms. The water present with other ingredients such as formic acid is simultaneously distilled during alkanoate formation in the presence of sufficient oxygen-containing gas to prevent the copper from plating on the distillation equipment. The mixture of cupric and manganous alkanoates recovered can be used as oxidation catalysts and especially in the production of $C_5$–$C_9$ saturated aliphatic monocarboxylic acids from their corresponding aldehydes.

The aqueous phase containing a mixture of copper and manganese formates is obtained from the aqueous formic acid extraction of a mixture of copper and manganese compounds used as an oxidation catalyst. A second phase is a water-immiscible organic phase comprising a saturated aliphatic monocarboxylic acid containing 5 to 9 carbon atoms produced by the oxidation of the corresponding aldehyde. The extraction process is described in copending application Ser. No. 466,447 previously mentioned.

The aqueous formic acid added to the organic phase comprising copper, manganese and monocarboxylic acid contains about 2 to about 20 weight percent formic acid, preferably about 4 to about 15 weight percent formic acid. The amount of formic acid added is sufficient to react with substantially all of the copper and manganese metal ions present. At least a molar equivalent of formic acid to the metal ions is required and an excess of formic acid is preferred. The volume ratio of the organic monocarboxylic acid to aqueous formic acid should exceed about 1 to 10, and is preferably about 10/1 to about 30/1. If an excess amount of formic acid is used and part of the acid remains in the organic monocarboxylic acid after separation from the aqueous phase, mixing an additional amount of water with the organic monocarboxylic acid will readily remove the excess formic acid because of its high solubility in water. It is desired to operate the extraction at ambient temperatures to save energy requirements although higher temperatures can be used with the disadvantage that as the temperatures increase the organic monocarboxylic acids can become more soluble in the aqueous phase and additional acids can be lost in the recovery system.

During and after the extraction of cupric and manganous formates from the organic monocarboxylic acid into the aqueous phase, two distinct phases readily form, an organic phase containing the monocarboxylic acid and an aqueous phase. The organic phase substantially free of the copper and manganous metal ions can be separated from the aqueous phase containing the copper and manganese. The recovered organic monocarboxylic acid can be then further purified by distillation. The copper and manganese metal ions can be recovered from the aqueous formic acid layer according to the process of this invention.

In accordance with this invention, the saturated organic monocarboxylic acids containing 5 to 9 carbon atoms which can be used in the recovery of the copper and manganese metal ions include n-octanoic acid, heptanoic acid, nonanoic acid, valeric acid, and isomers of these acids.

The reaction of the copper and manganese metal ions in the presence of water with a saturated organic monocarboxylic acid containing 5 to 9 carbon atoms can be carried out at temperatures in the range from about 190° C. to about 240° C., preferably from about 200° C. to about 220° C. for a sufficient period of time to complete the reaction. The reaction can take place in a distillation unit wherein the reboiler temperatures can be maintained above about 190° C. to insure the complete conversions of the copper and manganese compounds such as manganous formate and cupric formate to their respective alkanoates containing 5 to 9 carbon atoms.

While the cupric and manganese alkanoates are produced, the water present as well as other ingredients such as formic acid are simultaneously removed by distillation or flashing from the alkanoates. During distillation or flashing, a sufficient amount of oxygen is passed through the monocarboxylic acid/alkanoate mixture to prevent plating of the copper present in the distillation mixture. Manganese in the monocarboxylic acid does not reduce as readily as copper and therefore does not give rise to a plating out problem. Oxygen can be supplied in the form of air, as the substantially pure gas, or in other combinations with inert gases such as nitrogen. The function of the added oxygen is to keep the copper in an oxidation environment, thus preventing reduction to Cu+ which results in copper metal plating. The amount of oxygen required to prevent copper plating is a function of temperature, copper concentration and gas sparging efficiency. The amount of air which can be passed through the alkanoate product during distillation to prevent plating out of the copper on the distillation equipment is about 0.015 to about 0.7 standard cubic feet of air per pound of alkanoate product. If copper plates on the equipment during the distillation, an increase in the oxygen supply will redissolve the copper. An excess of oxygen is not detrimental to the distillation process. However, an excessive amount of oxygen passing through the aqueous alkanoate product will require additional energy requirements to maintain the equilibrium of the distillation process.

Any of several distillation procedures can be used in the separation of water and other ingredients such as formic acid, from the cupric and manganous alkanoates containing 5 to 9 carbon atoms. The water and other volatile ingredients can be flashed from the mixed alkanoates which can be then further purified for use as oxidation catalyst to produce a saturated aliphatic monocarboxylic acid having 5 to 9 carbon atoms from its corresponding aldehyde. Any standard distillation means can be used in the water-alkanoate separation.

The invention will be illustrated by the following examples:

EXAMPLES

A one-inch diameter ten stage York-Scheibel countercurrent extraction column was used for the continuous extraction of heptanoic and nonanoic oxidation products containing manganese and copper with aqueous formic acid. The column was operated with a two staged addition of aqueous formic acid, one at the lower end of the column and another at the upper end of the column to improve extraction efficiency. The staged addition of formic acid is required to minimize back extraction of formic acid into the organic phase. In an effort to help minimize this back extraction, the column was operated with the aqueous phase as the continuous phase as well as employing a water wash at the top of the extraction column.

Reference is made to the drawing which schematically depicts an Extraction Column. Organic feed is transmitted through line 10 into the lower stage 12 to the extraction column 11 having ten stages (12–21), each stage containing a paddle 30, distributed throughout the column 11 and a stirrer 22 containing a shaft 29 which passes through the ten stages. Each of the stages contain a calming zone 28 consisting of a packing such as stainless steel wire mesh, course glass wool, and the like. Aqueous formic acid is added to the column 11 in two stages: one through line 25 into stage 13 and the other through line 26 into stage 17. Water is fed through line 27 into stage 21. The organic phase containing the organic $C_5$–$C_9$ saturated aliphatic monocarboxylic acid is taken off at the top of the column at line 23 to be purified further by distillation and the aqueous phase containing the manganese and copper is removed at the bottom of the column at line 24 which can be treated further to recover the manganese and copper catalysts.

The operating conditions used for the York-Scheibel columns are listed as follows in Table I:

TABLE I

| | |
|---|---|
| Phasing time per stage* | 4 minutes |
| Mixing time per stage** | 1.5 minutes |
| Temperature | Room Temp. (25° C.) |
| Pressure | Atmospheric |
| Total aqueous formic acid feed rate | 0.6 milliliter/min. |
| Water feed rate | 0.3 milliliter/min. |
| Organic feed rate | 9 milliliter/min. |
| Continuous phase | Aqueous |

\* $\frac{\text{stage volume}}{\text{Total flow rate}}$
\*\* $\frac{\text{mixing volume}}{\text{Total flow rate}}$

EXAMPLE I

Using the York-Scheibel extraction column previously described and the operating conditions of Table I, nonanoic acid oxidation product containing manganese and copper metal ions, was extracted with aqueous formic acid, in two separate extractions. The feeds used and the products obtained are shown in Tables II and III.

TABLE II

Nonanoic Acid Extraction

| Stream | wt (g) | Cu g | Cu PPM | Mn g | Mn PPM | H$_2$O g | H$_2$O wt % | Formic Acid g | Formic Acid wt % |
|---|---|---|---|---|---|---|---|---|---|
| Organic Feed | 3637 | 0.7 | 200 | 0.6 | 160 | 3.6 | 0.1 | 0 | — |
| Formic Acid Feed | 257 | 0 | <1 | 0 | <1 | 237.0 | — | 20 | 7.8 |
| Water Feed | 152 | 0 | — | 0 | — | 152.0 | — | 0 | — |
| Organic Product (nonanoic Acid) | 3709 | 0 | 2 | 0 | <1 | 77.9 | 2.1 | (3.1)* | — |
| Aqueous Product | 302 | 0.7 | 2400 | 0.7 | 2200 | 283.9 | — | 15.1 | 5.0 |
| Accountability (%) | 99 | 100 | | 117 | | 92 | | — | |

*Value assumed by difference after accounting for metal formates.

TABLE III

Nonanonic Acid Extraction

| Stream | wt (g) | Cu g | Cu PPM | Mn g | Mn PPM | H$_2$O g | H$_2$O wt % | Formic Acid g | Formic Acid wt % |
|---|---|---|---|---|---|---|---|---|---|
| Organic Feed | 3656 | 0.7 | 200 | 0.6 | 160 | 0 | <0.1 | 0 | — |
| Formic Acid Feed | 284 | 0 | <1 | 0 | <1 | 262.1 | — | 29.1 | 7.7 |
| Water Feed | 147 | 0 | — | 0 | — | 147.0 | — | 0 | — |
| Organic Product (Nonanoic Acid) | 3750 | 0 | 1 | 0 | <1 | 75.0 | 2.0 | (0.8)$^a$ | — |
| Aqueous | 308 | 0.7 | 2400 | 0.8 | 2800 | 285.5 | — | 18.8 | 6.1 |
| Accountability (%) | 99 | 100 | | 130 | | 88 | | — | |

$^a$Value assumed by difference after accounting for metal formates.

EXAMPLE II

Using the York-Scheibel extraction column previously described and the operation conditions of Table I, heptanoic acid oxidation product containing manganese and copper metal ions, was extracted with aqueous formic acid, in two separate extractions. The feeds used and the products obtained are shown in Tables IV and V.

TABLE IV

Heptanoic Acid Extraction

| Stream | wt (g) | Cu g | Cu PPM | Mn g | Mn PPM | H$_2$O g | H$_2$O wt % | Formic Acid g | Formic Acid wt % |
|---|---|---|---|---|---|---|---|---|---|
| Organic Feed | 3649 | 0.8 | 220 | 0.8 | 210 | 3.6 | 0.1 | — | — |
| Formic Acid Feed | 278 | 0 | <1 | 0 | <1 | 242.2 | — | 35.8 | 12.9 |
| Water Feed | 353 | 0 | — | 0 | — | 353.0 | — | — | — |
| Organic Product (heptanoic acid) | 3871 | 0 | <1 | 0 | <1 | 174.0 | 4.5 | (13.8)$^a$ | — |
| Aqueous Product | 332 | 0.7 | 2100 | 0.7 | 2000 | 310.7 | — | 19.9 | 6.0 |
| Accountability (%) | 98 | 88 | | 88 | | 81 | | — | |

$^{(a)}$Value assumed by difference after accounting for metal formates.

TABLE V

Heptanoic Acid Extraction

| Stream | wt (g) | Cu g | Cu PPM | Mn g | Mn PPM | H₂O g | H₂O wt % | Formic Acid g | Formic Acid wt % |
|---|---|---|---|---|---|---|---|---|---|
| Organic Feed | 2596 | 0.5 | 210 | 0.5 | 210 | 0 | <0.1 | 0 | — |
| Formic Acid Feed | 278 | 0 | <1 | 0 | 1 | 240.7 | — | 37.3 | 13.4 |
| Water Feed | 51 | 0 | — | 0 | — | 51.0 | — | 0 | — |
| Organic Product (heptanoic acid) | 2726 | 0 | 2 | 0 | <1 | 114.5 | 4.2 | (28.1)[a] | — |
| Aqueous Product | 143 | 0.4 | 2500 | 0.4 | 2500 | 134.2 | — | 8.0 | 5.6 |
| Accountability (%) | 98 | 80 | | 80 | | 85 | | — | |

[a] Value assumed by difference after accounting for metal formates.

EXAMPLE III

The composite of the aqueous products of Tables II and III containing copper, manganese, formic acid and slightly larger volume of nonanoic acid were fed to a "flasher" which is a continuous one stage glass distillation column. The flasher operating conditions are shown in Table VI:

TABLE VI

| | |
|---|---|
| pressure | atmospheric |
| preheater temperature | 105° C. |
| overhead temperature | 110° C. |
| reboiler temperature | 205° C. |
| nonanoic acid feed rate | 4.5 milliliters/min. |
| aqueous feed rate | 4 milliliters/min. |
| base take off rate | 4 milliliters/min. |
| air bleed through liquid | 0.5 standard cubic feet/hour |

The water and formic acid were flashed overhead. The base take-off stream contained approximately 3000 parts per million each of copper and manganese as metal nonanoates in nonanoic acid solvent. In the flashing process, the metal formates were converted into cupric and manganous nonanoates. Proton transfer from nonanoic acid to formate can be realized at high temperatures, at least 190° C., preferably greater than 200° C.

The aqueous flasher overhead stream is suitable for recycle to the extractor as aqueous formic acid feed for removal of the copper and manganese compounds from the saturated aliphatic monocarboxylic acids. Approximately 50 percent of the formic acid can be recycled. The remainder of the formic acid is lost by back extraction into the organic phase (catalyst free saturated aliphatic monocarboxylic acid) in the extraction column. To minimize the impact of the formic acid loss, it is recommended that only a small excess (approximately 300%) of formic acid be used in the extraction column. Using approximately a 4 weight percent formic solution in the extraction would accomplish the desired result.

An air bleed is required in the flasher reboiler to prevent the copper plating.

Using the conditions described above in the distillation procedure, cupric and manganous nonanoates in nonanoic acid were obtained in the base take off product from the aqueous formic acid solution. The feeds used and the products obtained are described in Table VII.

TABLE VII

Flasher Mass Balance for Nonanoic Acid

| Stream | wt (g) | Cu g | Cu PPM | Mn g | Mn PPM | H₂O g | H₂O wt % | Formic Acid g | Formic Acid wt % | Nonanoic Acid g | Nonanoic Acid wt % |
|---|---|---|---|---|---|---|---|---|---|---|---|
| Organic Feed | 1647 | 0 | 0 | 0 | 0 | 29.7 | 1.8 | 0 | 0 | 1617.3 | — |
| Aqueous Feed | 1386 | 3.6 | 2600 | 4.6 | 3300 | 1322.4 | — | 55.4 | 4.0 | 0 | — |
| Base Take-Off | 1556 | 2.2 | 1400 | 4.5 | 2900 | 3.1 | 0.2 | 0 | — | 1546.2 | — |
| Overhead Organic | 95 | 0 | 1 | 0 | 1 | 0.1 | 0.1 | (15.3)[a] | — | 80.6 | — |
| Overhead Aqueous | 1378 | 0 | 1 | 0 | 1 | 1311.8 | — | 52.4 | 3.8 | 13.8 | 1.0 |
| Accountability (%) | 100 | 61[b] | | 98 | | 97 | | 101.0 | | 101.0 | |

[a] Value assumed by difference. Also includes formic acid generated from metal formates.
[b] The low accountability may be due to a sampling problem.

EXAMPLE IV

The composite of the aqueous products of Tables IV and V containing copper, manganese/formic acid and slightly larger volume of heptanoic acid were fed to a flasher which is a continuous one stage glass distillation column.

The flasher operating conditions are shown in Table VIII:

TABLE VII

| | |
|---|---|
| pressure | 1 atmosphere |
| preheater temperature | 105° C. |
| overhead temperature | 130° C. |
| reboiler temperature | 200° C. |
| heptanoic acid feed rate | 5 milliliters/min |
| aqueous feed rate | 4 milliliters/min. |
| base take-off rate | 4.5 milliliters/min. |
| air bleed | 0.5 standard cubic feet per hour |

Using the above conditions in the distillation procedure, cupric and manganous heptanoates in heptanoic acid were obtained in the base take off product from the aqueous formic acid solution. The feeds used and the products obtained are described in Table IX:

TABLE IX

Flasher Mass Balance for Heptanoic Acid Run

| Stream | wt (g) | Cu g | Cu PPM | Mn g | Mn PPM | H₂O g | H₂O wt % | Formic Acid g | Formic Acid wt % | Heptanoic Acid g | Heptanoic Acid wt % |
|---|---|---|---|---|---|---|---|---|---|---|---|
| Organic Feed | 1018 | 0 | 1 | 0 | 1 | 0 | — | 0 | — | 1018 | — |
| Aqueous Feed | 698 | 2.5 | 3600 | 2.4 | 3400 | 663.1 | — | 30 | 4.3 | 0 | — |
| Base Take-Off | 840 | 2.5 | 3000 | 2.3 | 2700 | 0.8 | 0.1 | 0 | — | 834.4 | — |
| Overhead Organic | 143 | 0 | 1 | 0 | 1 | 8 | 5.6 (9.2)$^a$ | — | 125.8 | — | |
| Overhead Aqueous | 688 | 0 | 1 | 0 | 1 | 654.3 | — | 28.2 | 4.1 | 5.5 | 0.8 |
| Accountability (%) | 97 | | 100 | | 96 | | 100 | | — | | 95 |

$^a$Value assumed by difference. Also includes formic acid generated from metal formates.

The cupric and manganous heptanoates in heptanoic acid in the tower bottoms take-off product, can be used as oxidation catalysts by recycling the heptanoates to the heptanal oxidation reactor to produce heptanoic acid.

What is claimed is:

1. A process for recovering water soluble cupric and manganous compounds present in water which comprises reacting a saturated aliphatic monocarboxylic acid containing 5 to 9 carbon atoms with said cupric and manganous compounds at temperatures about 190° C. to form cupric and manganous alkanoates containing 5 to 9 carbon atoms, and simultaneously removing the water by distillation in the presence of sufficient oxygen-containing gas to prevent the copper from plating on the distillation equipment and recovering said cupric and manganous alkanoates.

2. The process of claim 1 wherein the reaction temperature is about 200° C. to about 220° C.

3. The process of claim 1 wherein the saturated aliphatic monocarboxylic acid is heptanoic acid.

4. The process of claim 1 wherein the saturated aliphatic monocarboxylic acid is nonanoic acid.

5. In a process for producing a saturated aliphatic monocarboxylic acid containing 5 to 9 carbon atoms by the oxidation of its corresponding aldehyde in the presence of a catalyst containing the combination of manganous and cupric ions, the improvement comprising removing said manganous and cupric ions from said monocarboxylic acid by adding an aqueous formic acid solution containing from about 2 to about 20 weight percent formic acid in an amount such that the volume ratio of said monocarboxylic acid to aqueous formic acid exceeds about 1 to 10 to form cupric formate and manganous formate in an aqueous phase in contact with a water-immiscible organic phase containing said monocarboxylic acid; separating said aqueous and water-immiscible organic phases; removing said monocarboxylic acid substantially free of copper and manganese in said organic phase; reacting said cupric and manganous ions with a saturated aliphatic monocarboxylic acid containing 5 to 9 carbon atoms at a temperature from about 190° C. to about 240° C. to form cupric and manganous alkanoates containing 5 to 9 carbon atoms; and simultaneously removing the water and formic acid by distillation in the presence of a sufficient amount of oxygen-containing gas to prevent copper from plating out on the distillation equipment and recovering said cupric and manganous alkanoates.

6. The process of claim 5 wherein heptanoic acid is produced by the catalytic oxidation from heptanal; heptanoic acid is reacted with the cupric and manganous formate to form cupric heptanoate and manganous heptanoate which are recycled as the catalysts for the oxidation of heptanal to heptanoic acid.

7. The process of claim 5 wherein nonanoic acid is produced by the catalytic oxidation from nonanal; nonanoic acid is reacted with cupric and manganous formate to form cupric nonanoate and manganous nonanoate which are recycled as the catalysts for the oxidation of nonanal to nonanoic acid.

* * * * *